(12) United States Patent
Barkholt et al.

(10) Patent No.: US 10,383,790 B2
(45) Date of Patent: Aug. 20, 2019

(54) EYE OPENING DEVICE

(71) Applicant: Plum A/S, Assens (DK)

(72) Inventors: Bo Winther Barkholt, Assens (DK); Per Pasfall, Assens (DK); Poul Bertelsen, Assens (DK); Bue Blinkenberg, Assens (DK)

(73) Assignee: Plum A/S, Assens (DK)

( * ) Notice: Subject to any disclaimer, the term of this patent is extended or adjusted under 35 U.S.C. 154(b) by 96 days.

(21) Appl. No.: 15/488,949

(22) Filed: Apr. 17, 2017

(65) Prior Publication Data

US 2017/0296430 A1   Oct. 19, 2017

(30) Foreign Application Priority Data

Apr. 18, 2016  (EP) .................................... 16165801

(51) Int. Cl.
| | |
|---|---|
| *A61B 17/02* | (2006.01) |
| *A61H 35/02* | (2006.01) |
| *A61F 9/00* | (2006.01) |
| *B05B 12/16* | (2018.01) |

(52) U.S. Cl.
CPC ........... *A61H 35/02* (2013.01); *A61F 9/0026* (2013.01); *B05B 12/40* (2018.02)

(58) Field of Classification Search
CPC ....... A61B 1/32; A61B 17/02; A61B 17/0231; A61F 9/0026; A61F 9/0008; A61H 35/02; A61M 2210/0612; A61M 11/00
See application file for complete search history.

(56) References Cited

U.S. PATENT DOCUMENTS

| | | | | |
|---|---|---|---|---|
| 3,934,590 A | * | 1/1976 | Campagna ............ | A61F 9/0026 604/302 |
| 4,085,750 A | * | 4/1978 | Bosshold .............. | A61F 9/0026 604/302 |
| 5,064,420 A | * | 11/1991 | Clarke .................. | A61F 9/0026 604/295 |
| 5,387,202 A | * | 2/1995 | Baron ................... | A61F 9/0026 604/300 |
| 5,433,190 A | * | 7/1995 | Sunalp ............... | A61B 17/0231 600/236 |
| 6,736,802 B1 | * | 5/2004 | Recanati ............... | A61F 9/0008 222/420 |
| D672,870 S | * | 12/2012 | Bertelsen ............. | A61F 9/0026 D24/120 |
| 9,610,192 B2 | * | 4/2017 | Marx .................... | A61F 9/0026 |
| 2006/0282049 A1 | * | 12/2006 | Lee ....................... | A61F 9/0026 604/300 |

(Continued)

FOREIGN PATENT DOCUMENTS

EP   0 998 895 A1   5/2000

*Primary Examiner* — Eduardo C Robert
*Assistant Examiner* — Michelle C Eckman
(74) *Attorney, Agent, or Firm* — McCormick, Paulding & Huber LLP (57) ABSTRACT

For allowing an access to an eye during a rinsing process it is suggested to configure an eye opening device in such a way that the eye opening device comprises two wing-like spreading elements for pulling the upper eyelid and the lower eyelid of the eye apart so as to support the opening of the eye during a rinsing process, wherein two access gaps are formed laterally between the two wing-like spreading elements of the eye opening device.

11 Claims, 5 Drawing Sheets

(56) References Cited

U.S. PATENT DOCUMENTS

| | | | | |
|---|---|---|---|---|
| 2009/0259204 A1* | 10/2009 | Galdeti | ............ | A61F 9/0026 |
| | | | | 604/302 |
| 2010/0022971 A1* | 1/2010 | Marx | ............ | A61F 9/0026 |
| | | | | 604/302 |
| 2010/0286633 A1* | 11/2010 | Marx | ............ | A61F 9/0026 |
| | | | | 604/296 |
| 2010/0286634 A1* | 11/2010 | Marx | ............ | A61F 9/0026 |
| | | | | 604/302 |
| 2011/0106024 A1* | 5/2011 | Katayama | ............ | A61F 9/0008 |
| | | | | 604/294 |
| 2012/0071840 A1* | 3/2012 | Bertelsen | ............ | A61H 35/02 |
| | | | | 604/302 |
| 2015/0065809 A1* | 3/2015 | Assia | ............ | A61B 17/0231 |
| | | | | 600/217 |
| 2015/0088099 A1* | 3/2015 | Lorch | ............ | A61F 9/0026 |
| | | | | 604/521 |
| 2017/0196732 A1* | 7/2017 | Marx | ............ | A61F 9/0026 |
| 2017/0224532 A1* | 8/2017 | Behan | ............ | A61F 9/0008 |
| 2017/0296430 A1* | 10/2017 | Barkholt | ............ | B05B 12/40 |
| 2017/0319385 A1* | 11/2017 | Fresco | ............ | A61F 9/0026 |
| 2018/0042597 A1* | 2/2018 | Assia | ............ | A61B 17/0231 |

* cited by examiner

EYE OPENING DEVICE

CROSS-REFERENCE TO RELATED APPLICATION

This application claims foreign priority benefits under U.S.C. § 119 to European Patent Application No. 16165801.8 filed on Apr. 18, 2016, the content of which is hereby incorporated by reference in its entirety.

TECHNICAL FIELD

The invention relates to an eye opening device as well as an eye rinsing device.

BACKGROUND

Eye opening devices are known from prior art. Those eye opening device typically comprise an eye cup for forcing the eye open during a rinsing process. For example, EP 0,998 895 A1 describes an eye wash device having an eye cup with an annular contact surface which can engage with the eye socket around the eye of a patient so that the eyelids are eccentrically widened by pressure loading.

However, the use of an eye cup has several disadvantages, one being that the eyecup shields the eye to a very high degree, so that there is no possibility of either observing the rinsing process or helping it in any way.

SUMMARY

It is an objective of the present invention to improve an eye opening device in such a way that a rinsing process of an eye is simplified, especially by making it possible that either the user of the eye opening device himself or another person can actively help the rinsing processing.

The above objective is solved by providing an eye opening device for opening an eye with an upper eyelid and a lower eyelid such that the eye can be rinsed. The eye opening device comprises two wing-like spreading elements for pulling the upper eyelid and the lower eyelid of the eye apart so as to support the opening of the eye during a rinsing process, wherein the wing-like spreading elements are configured such that two access gaps for allowing an access to the eye during the rinsing process are formed laterally between the wing-like spreading elements. Preferably, the access gaps also allow an access to the surrounding part of the eye, such as the eye socket and/or the eye lids.

The eye opening device serves to artificially keep the eye lids of an eye apart during a rinsing process. The eye opening device can be used for medical purposes, e.g. after an eye has come into contact with chemicals, such as e.g. acids. Furthermore, the eye opening device can be used for eye refreshment purposes, e.g. in very dry air so that the eye feels uncomfortably dry or when it has come into contact with dust or dirt. Also for people suffering from pollen allergy it can be very comfortably to rinse the typically itching eyes using the eye opening device.

When the eye opening device is used, it is pressed onto an eye socket of an eye in such a way that the eye lids are pulled apart and the eye is forced open. However, especially, when a person is in pain or in a stressful situation, it can be very hard for him to keep the eyes open despite of the eye opening device. Furthermore, the eye closes reflexively, when a rinsing fluid is sprayed onto it. In other words, the person could resist either actively or reflexively against the artificial opening of the eye opening device which would make a successful eye rinsing process difficult.

The eye opening device according to the present invention provides two wing-like spreading elements which act as two artificial fingers for opening the eye by spreading the upper and the lower eye lid apart. However, to ensure that the rinsing process is successful, the wing-like spreading elements are configured such that two access gaps are formed laterally between the wing-like spreading elements. Each access gap allows access to the eye during the rinsing process.

In particular, each access gaps is configured such that a person can reach through it for helping the rinsing process. In particular, the access gaps are formed such that a person can reach through each of the access gaps with at least one finger, preferably two fingers. This person can either be the user of the eye opening device, i.e. the person onto whose eye the eye opening device is used, or another helping person. Especially, regarding a helping person the access gaps make an observation of the eye rinsing process possible, especially of the correct opening of the eye. The helping person can determine whether the eye opening device is used correctly and the eye is sufficiently wide opened. Furthermore, a person (again either the user of the eye opening device or another helping person) can reach trough an access gap, in particular with two fingers, to assist the opening process of the eye and thus the rinsing process. As a consequence, a helping person can first observe and then, if necessary, intervene and help.

Another advantage of the access gaps is that rinsing fluid can optimally drain without contaminating the eye opening device so that the eye opening device can be used multiple times.

Preferably, the eye opening device defines a space between the wing-like spreading elements. In particular, each access gap is formed such that it allows an access to this space.

Advantageously, the eye opening device comprises a cap-like portion, wherein the cap-like portion comprises at least one rinsing opening for letting rinsing fluid pass towards an eye to be rinsed. In particular, the rinsing opening is configured such it aims directly towards the eye, especially the pupil and/or the surroundings of the eye, such as the tear duct. The cap-like portion has the shape of a cap or in other words lid. The cap-like portion especially comprises a substantially closed end in longitudinal direction of the eye opening device, except for the rinsing opening which is preferably disposed at this closed end, in particular in the central part of this end. The wing-like spreading elements and the cap-like portion are preferably formed in one piece.

The eye opening device is especially configured as an attachment for an eye rinsing device. The attachment can preferably be attached onto an eye rinsing bottle containing rinsing fluid for eyes. The bottle can be configured squeezable such that when being squeezed rinsing fluid from the bottle exits the eye opening device through the rinsing opening. Alternatively, the bottle can be pressurized such that when an actuator is being pressed rinsing fluid is forced out of the rinsing opening of the eye opening device. Such a bottle is typically a spray can.

Preferably, the eye opening device is configured such that it can be screwed, pressed or pushed onto an eye rinsing bottle or can. In both ways, the eye opening device and/or the rinsing bottle are configured such that the discharge of rinsing fluid through the rinsing opening can be caused by one hand only.

Advantageously, each wing-like spreading element has a first end area being attached to the cap-like portion and a second end area comprising a free end of the wing-like spreading element. The first end area and/or the second end area are configured in a curved way, especially in a longitudinal section of the wing-like spreading element. In particular, the wing-like spreading elements are disposed such that they are not connected to each other except for via the cap-like portion. In this way, the reaching gaps are formed laterally throughout the entire length of the wing-like spreading elements.

Especially, each wing-like spreading element is curved in its first end area in such a way that an imaginary secant line between two points within the first end area is disposed such that it faces the other wing-like spreading element. A secant line is a line which connects two points on a curve. The imaginary secant line is formed linearly, i.e. without any curves. The imaginary secant line in the first end area connects two points of the first end area which are located at different lengthwise positions regard-ing the length of the wing-like spreading element. The first end areas of the wing-like spreading elements are curved such that the wing-like spreading elements preferably merge, at least optically via a part of the cap-like portion, into each other in the central part of the cap-like portion. In particular, the wing-like spreading elements are configured equally.

In the second end area each wing-like spreading element is preferably curved in such a way that an imaginary secant line between two points within the second end area is disposed such that it faces away from the other wing-like spreading element.

Further preferred, each wing-like spreading element has a first side being directed towards the other wing-like spreading element and a second side being directed away from the other wing-like spreading element. In other words, the first side corresponds to a first surface and the second side to a second surface of the wing-like spreading element. The imaginary secant line in the first end area of a wing-like spreading element is preferably disposed such that it faces the first side of the same and the other wing-like spreading element, while the imaginary secant line on the second end area is disposed facing the second side of the same wing-like spreading element.

Preferably, each wing-like spreading element comprises two longitudinal edges extending along the length of the wing-like spreading element. The two access gaps are in particularly disposed between the wing-like spreading elements laterally, i.e. between one longitudinal edge of one wing-like spreading element and the opposing longitudinal edge of the other wing-like spreading element, respectively.

Between the first end area and the second end area the eye opening device particularly comprises a middle area which is configured linearly. In other words, the middle area is configured straight and does not comprise any curves. Preferably, the wing-like spreading elements consist only of the first end area, the second end area and the middle area.

Preferably, each wing-like spreading element comprises a furthest point in the second end area being furthest away from the first end area of the wing-like spreading element, said furthest point not being the free end of the wing-like spreading element. In other words, the curvatures of the second area is thus extensive that the free end of the wing-like spreading element is disposed closer to the first end area of the wing-like spreading element than the furthest point. Due to the extensive curvature of the second end area a rolling contacting process is ensured when the wing-like spreading elements are pressed onto the surroundings, especially the eye lids or the eye socket, of an eye. This means that the second end area partly rolls on the part of the surroundings of an eye with which it comes into contact so that the opening process becomes softer and more comfortable. The described configuration thus guarantees a gentle but at the same time secure pulling apart movement of the eye lids.

The wing-like spreading element and/or the cap-like portion is formed from an elastic material such that when the eye opening device is used on an eye, each wing-like spreading element is deformed elastically such that the distance between the wing-like spreading elements, especially between their second end areas, increases which allows the opening of the eye. For allowing this elastic movement of the second end areas of the wing-like spreading elements with respect to the first end areas being fixed on the cap-like portion, each wing-like spreading element comprises a hinge point about which the second end areas can be pivoted.

Further preferred, each wing-like spreading element is supported in longitudinal direction of the eye opening device or in longitudinal direction of the wing-like spreading element by a lengthwise grove. The lengthwise grove extends preferably along the entire length of the first end area. The lengthwise grove is disposed on the second side of the wing-like spreading element. The lengthwise grove serves to support the wing-like spreading element in its first end area in such a way that the hinge point about which the second end area can be pivoted is disposed in the middle area of the respective wing-like spreading element.

Each wing-like spreading element is preferably configured such that the width of the wing-like spreading element in its second end area is greater than its width in its first end area and/or its width in its middle area. The width in the second end area is particularly at least 10%, preferred 15%, further preferred 20%, larger than the width in the first end area and/or the width in the middle area. At the free end of the wing-like spreading element the width can decrease minimally again owed to a rounded configuration of the free end. By configuring the width in the second end area broader a sufficient contact area for contacting the surroundings of any eye is provided. In particular, the pressure being exerted by means of the eye opening device is distributed on a contact area which is big enough for the pressure to be comfortable for the person onto whose eye the eye opening device is used. At the same time, by configuring the width of the wing-like spreading element as compared to the second end area smaller in its middle area and/or in its first end area a sufficiently big access gaps is provided such that the eye rinsing process can be observed and helped.

The length of first end area and/or the second end area (being projected onto the longitudinal axis of the eye opening device) particularly accounts for 10% to 30%, preferred 15% to 25%, most preferred 17.5% to 22.5%, of the length of wing-like spreading element (being projected to the longitudinal axis of the eye opening de-vice). When being referred to the actual length of the partly curved wing-like spread-ing element, the length of the end area accounts for 10% to 30%, preferred 15% to 25%, most preferred 17.5% to 22.5%. Referred to the actual length of the wing-like spreading element, the second end area has a length which is at least 15%, preferred at least 25%, most preferred at least 30%, greater than the length of the second end area (being projected onto the longitudinal axis of the eye opening device).

Preferably, the width of each wing-like spreading element, especially in its second end area, is smaller than the smallest outer diameter of the cap-like portion. The smallest outer diameter is preferably disposed at the substantially closed end of the cap-like portion comprising the rinsing opening. In particular, the width of the wing-like spreading element is smaller than 80% of the smallest outer diameter of the cap-like portion.

Advantageously, each wing-like spreading element comprises a contact area for contacting a surrounding of an eye, wherein the contact area comprises a slip-resistant surface structure. The contact area is preferably disposed on the first side of the wing-like spreading element facing the other wing-like spreading element. Further preferred, the contact surface is disposed in the second end area of the wing-like spreading element. The slip-resistant surface is preferably configured by small profiled bars, studs or the like for forming a slip-resistant profile.

Preferably, the cap-like portion comprises holding areas for holding the eye opening device, said holding areas comprising a slip-resistant surface structure. The holding areas are preferably disposed at a circumferential distance of 180° to each other. The holding areas are disposed at an outer surface of the cap-like portion. Furthermore, the holding areas are disposed in longitudinal direction of the eye opening device underneath the wing-like spreading elements. Alternatively, the holding areas can be disposed in longitudinal direction underneath the access gaps. The slip-resistant surface is preferably configured by small profiled bars, studs or the like for forming a slip-resistant profile.

Preferably, the holding areas are configured such that when being pressed an actuator of a rinsing bottle can be activated such that rinsing fluid is discharged from the rinsing opening.

The cap-like portion particularly comprises at least one sealing member. Furthermore, the cap-like portion comprises an interior space. Especially, the cap-like portion comprises a first end onto which the wing-like spreading elements are mounted and a second end which is preferably attachable to a rinsing bottle. The sealing member is particularly disposed at the second end of the cap-like portion protruding into an interior space of the cap-like portion. The sealing member serves to avoid rinsing fluid entering the interior space of the cap-like portion from its second end. The sealing member is advantageously formed as a circumferential sealing lip extending along the circumference of the cap-like portion at its second end.

Furthermore, the eye opening device preferably comprises a sealing member being disposed within the rinsing opening. This sealing member serves to ensure that used rinsing fluid cannot flow back into the rinsing bottle and thus possibly contaminate the rinsing fluid within the rinsing bottle which has not yet been used. Hence, by means of the sealing member a multiple use of the eye opening device or the respective eye rinsing device is made possible. The sealing member is advantageously formed as a circumferential sealing lip extending along the circumference of the rinsing opening.

In a further aspect, the invention concerns an eye rinsing device comprising an eye opening device as described above. The eye rinsing device preferably comprises an eye rinsing bottle containing rinsing fluid. Furthermore, the eye rinsing device is preferably configured such that it can be used in every orientation. The eye rinsing process can therefore be conducted positionally independent, especially with regard to the direction of the force of gravity.

BRIEF DESCRIPTION OF THE DRAWINGS

The invention will be described below with reference to the following figures which show in schematic representation.

DETAILED DESCRIPTION

Figure 1:
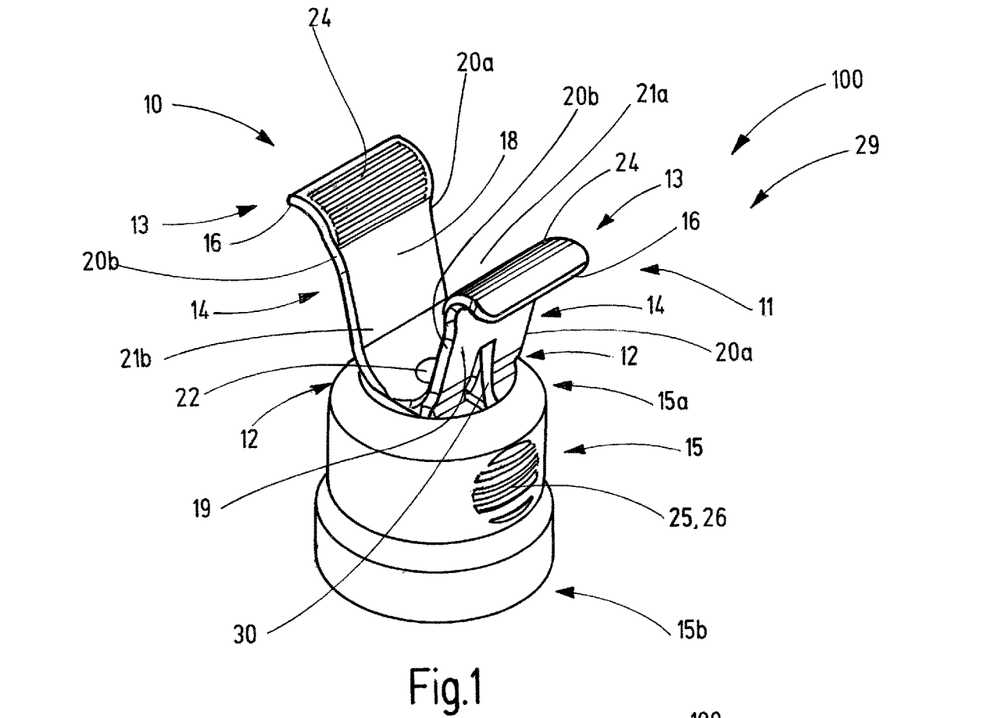
FIG. 1 is a perspective view on an eye opening device.

FIG. 1 shows a perspective view of an eye opening device (100) according to the invention. The eye opening device (100) is configured as an attachment (29) for an eye rinsing bottle (40) of an eye rinsing device (200). The eye opening device (100) comprises a cap-like portion (15) with a first substantially closed end (15a) and a sec- and open end (15b) which is attachable to an eye rinsing bottle (40). In the central part of the cap-like portion (15) at its first end (15a) a rinsing opening (22) is disposed. The cap-like portion (15) has the proximate shape of a hollow cylinder whose diameter may or may not be constant. In particular, the diameter at its second end (15b) is greater than the diameter at its first end (15a).

The eye opening device (100) comprises two wing-like spreading elements (10, 11), a first wing-like spreading element (10) and a second wing-like spreading element (11) being attached to the cap-like portion, especially at the first end (15a) of the cap-like portion (15). The wing-like spreading elements (10, 11) have a first end area (12) and a second end area (13). At the first end area (12) the wing-like spreading elements (10, 11) are attached to the cap-like portion, respectively. The second end areas (13) of each wing-like spreading element (10, 11) comprise a free end (16) of the respective wing-like spreading element (10, 11).

The wing-like spreading elements (10, 11) comprise a first side (18) being disposed towards the other wing-like spreading element (10, 11) and a second side (19) being the opposing side of the wing-like spreading (10, 11) and thus facing away from the other wing-like spreading element (10, 11). Hence, the first sides (18) of the two wing-like spreading elements (10, 11) face each other, while the second sides (19) are turned away respectively.

At its first sides (18) the wing-like spreading elements (10, 11) each comprise a con tact area (24) being characterized by a slip-resistant surface structure (26) for allowing a secure grip of a surrounding of an eye, especially the eye lids. The contact area (24) is disposed in the second end area (13). Furthermore, the cap-like portion (15) of the eye opening device (100) comprises two holding areas (25) for holding the eye opening device (100). The holding areas (25) are disposed at opposite sides of the cap-like portion, preferably underneath the wing-like spreading elements (10, 11).

Each wing-like spreading element (10, 11) comprises a lengthwise grove (30) extending in the first end area (12) at the second side (19) of the wing-like spreading element (10, 11). The lengthwise grove (30) extends along substantially the entire length (12a) of the first end area (12) being projected onto the longitudinal direction (31) of the eye opening device (100).

The wing-like spreading elements (10, 11) are formed such that two access gaps (21a, 21b) are formed laterally between the wing-like spreading elements (10, 11). Each wing-like spreading element (10, 11) has two longitudinal edges (20a, 20b). The access gaps (21a, 21b) are disposed between a longitudinal edge (20a, 20b) of the first wing-like spreading element (10) and the opposing longitudinal edge (20a, 20b) of the second wing-like spreading element (11).

Figure 2:
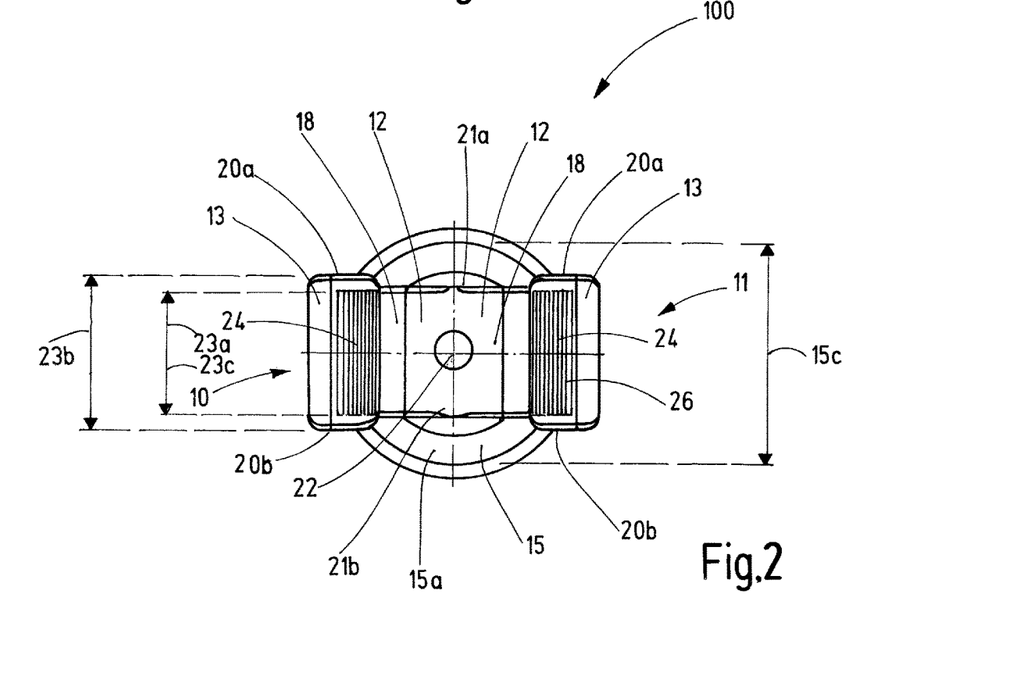
FIG. 2 is a top view on the eye opening device according to FIG. 1.

In FIG. 2 a top view on the eye opening device according to FIG. 1 is shown. The wing-like spreading elements (10, 11) have a width (23a) at their first end areas (12) and a width at their middle areas (14) which correspond to each other. However, the width (23b) at the second end area (13) at each wing-like spreading element (10, 11) is larger than the widths (23b, 23c) at the first end area (12) and the middle area (14). The cap-like portion (15) comprises a smallest outer diameter (15c) at its first end (15a). The smallest outer diameter (15c) is greater than the widths (23a, 23c, 23b) of the wing-like spreading elements (10, 11). The contact areas (24) extend in the second end area (13) along a length which corresponds to the width (23b) in the first end area (13).

The longitudinal edge (20a) of the first wing-like spreading element (10) faces the longitudinal edge (20a) of the second wing-like spreading element (11). In between these edges (20a), i.e. laterally between the wing-like spreading elements (10, 11) the access gap (21a) is disposed. The same applies to the longitudinal edges (20b), wherein also the longitudinal edge (20b) of the first wing-like spreading element (10) faces the longitudinal edge (20b) of the second wing-like spreading element (11) so that in between the access gap (21b) is formed.

Figure 3:
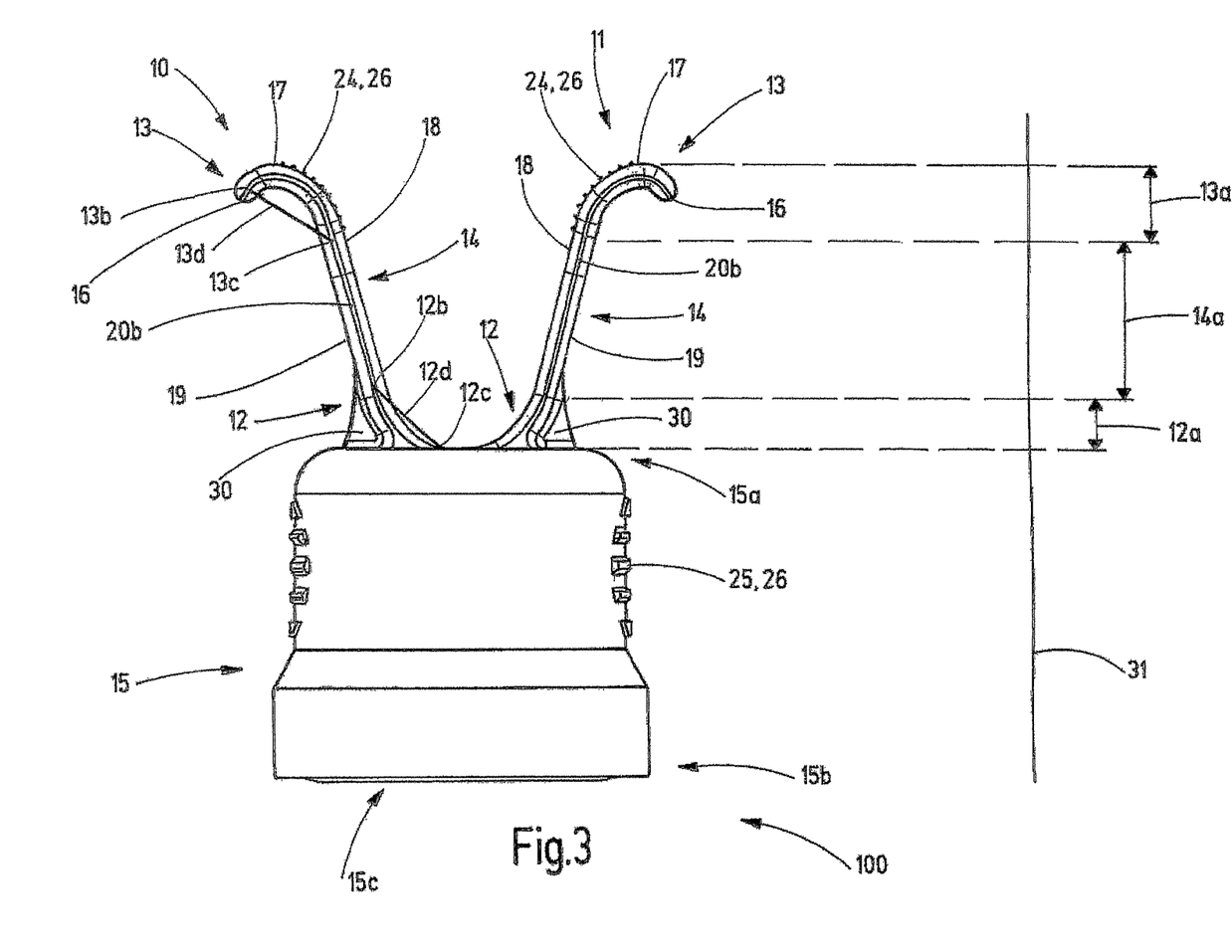
FIG. 3 is a side view on the eye opening device according to FIGS. 1 and 2.

In FIG. 3 a side view of an eye opening device (100) according to FIGS. 1 and 2 is shown. It can be clearly seen that the diameter of the cap-like portion is greater at its second end (15b) compared to its first end (15a). The holding areas (25) are disposed at opposite sides of the outer surface of the cap-like portion.

The wing-like spreading elements (10, 11) are formed such that the first end area (12) has a length (12a), the second end area (13) a length (13a) and the middle area (14) a length (14a), each projected onto the longitudinal direction (31) of the eye opening device (100). The length (12a) and the length (13a) are smaller than the length (14a).

In FIG. 3 the curvatures of the first end area (12) and the second end area (13) can well be seen. The second end area (13) is curved such that the furthest point (17) from the first end area (12) is not the free end (16). Exemplary two points (13b, 13c) have been drawn into FIG. 3 within the second end area (13) which are connected linearly by an imaginary secant line (13d). This secant line (13d) is disposed at the second side (19) of the wing-like spreading element (11) facing away from the other wing-like spreading element (10). In the first end area (12) also two exemplary points (12b, 12c) as well as a connecting secant line (12d) are shown. The secant line (12d) of the first end area (12) is disposed at the first side (18) of the wing-like spreading element (11) facing the other wing-like spreading element (10).

The lengthwise groves (30) supporting each wing-like spreading element (10, 11) in its first end area (12) extends along the entire length (12a) of the first end area (12). The slip-resistant surface structures (26) of the contact areas (24) and the holding areas (25) are formed by small profiled bars.

Figure 4:
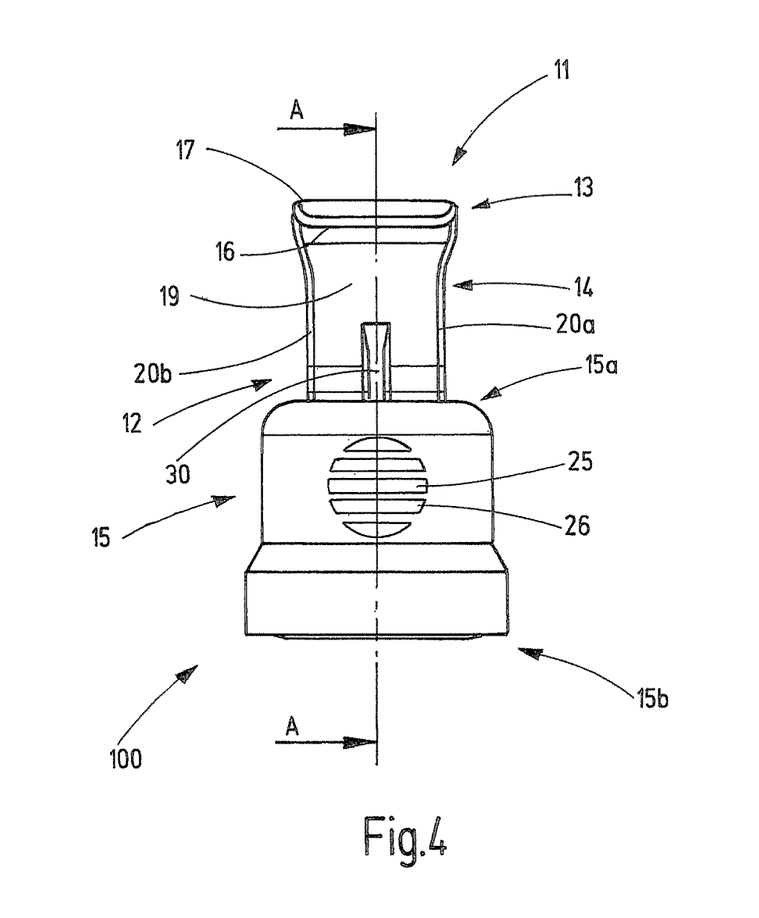
FIG. 4 is a side view on the eye opening device according to FIGS. 1 to 3.

FIG. 4 depicts a side view on the eye opening device according to FIGS. 1 to 3 which is rotated 90° compared to the side view of FIG. 3. It can well be seen that the free end (16) of each wing-like spreading element (10, 11) is configured slightly rounded. Furthermore, the furthest point (17) is disposed above the free end (16) in longitudinal direction (31) of the eye opening device (100). The width of the lengthwise grove (30) is about one fifth of the width (23a) of the wing-like spreading element (10, 11) in its first end area (12).

Figure 5:
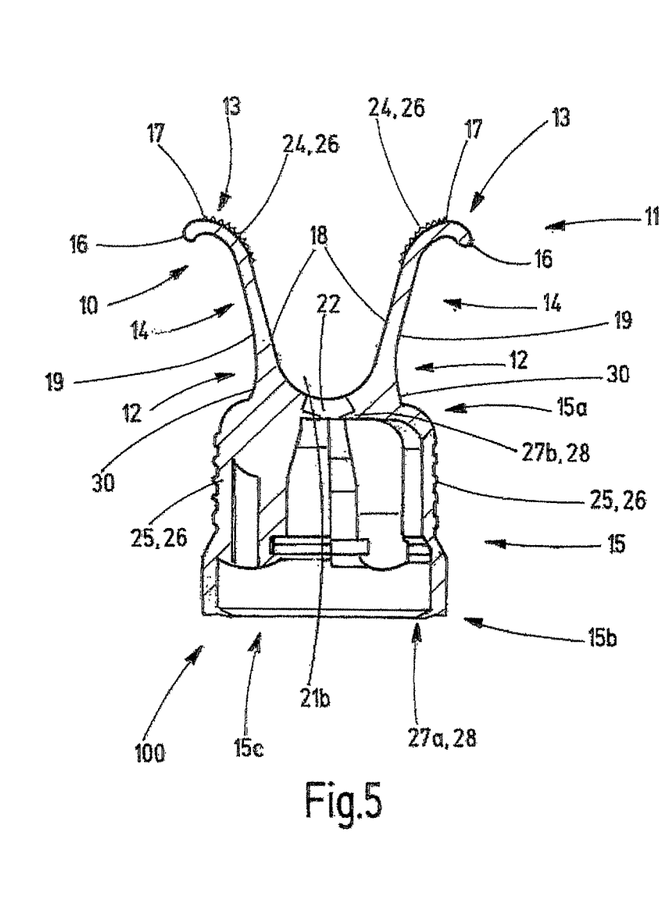
FIG. 5 is a view on a section along the cutting line A-A of FIG. 4.

In FIG. 5 a section along the cutting line A-A of FIG. 4 is shown. The cap-like portion (15) comprises an interior space (15d). Furthermore, it has the rinsing opening (22) at its first end (15a) and another opening (15e) at its second end (15b) for attachment to a rinsing bottle (40) of an eye rinsing device (200). At its second end the cap-like portion comprises a sealing member (27a) embodied by a sealing lip (28) ex-tending slightly into the interior space (15d) of the cap-like portion (15). The sealing member (27a) serves to seal the interior space (15d) of the cap-like portion (15) from its second end (15b) such that no rinsing fluid can enter the interior space (15d) from the second end (15b). Furthermore, the cap-like portion (15) comprises a sealing member (27b), namely a sealing lip (28), at its first end (15a). The sealing member (27b) is disposed at the rinsing opening (21) and serves to avoid that rinsing fluid flows into the interior space (15d) from the first end (15a).

Figure 6:
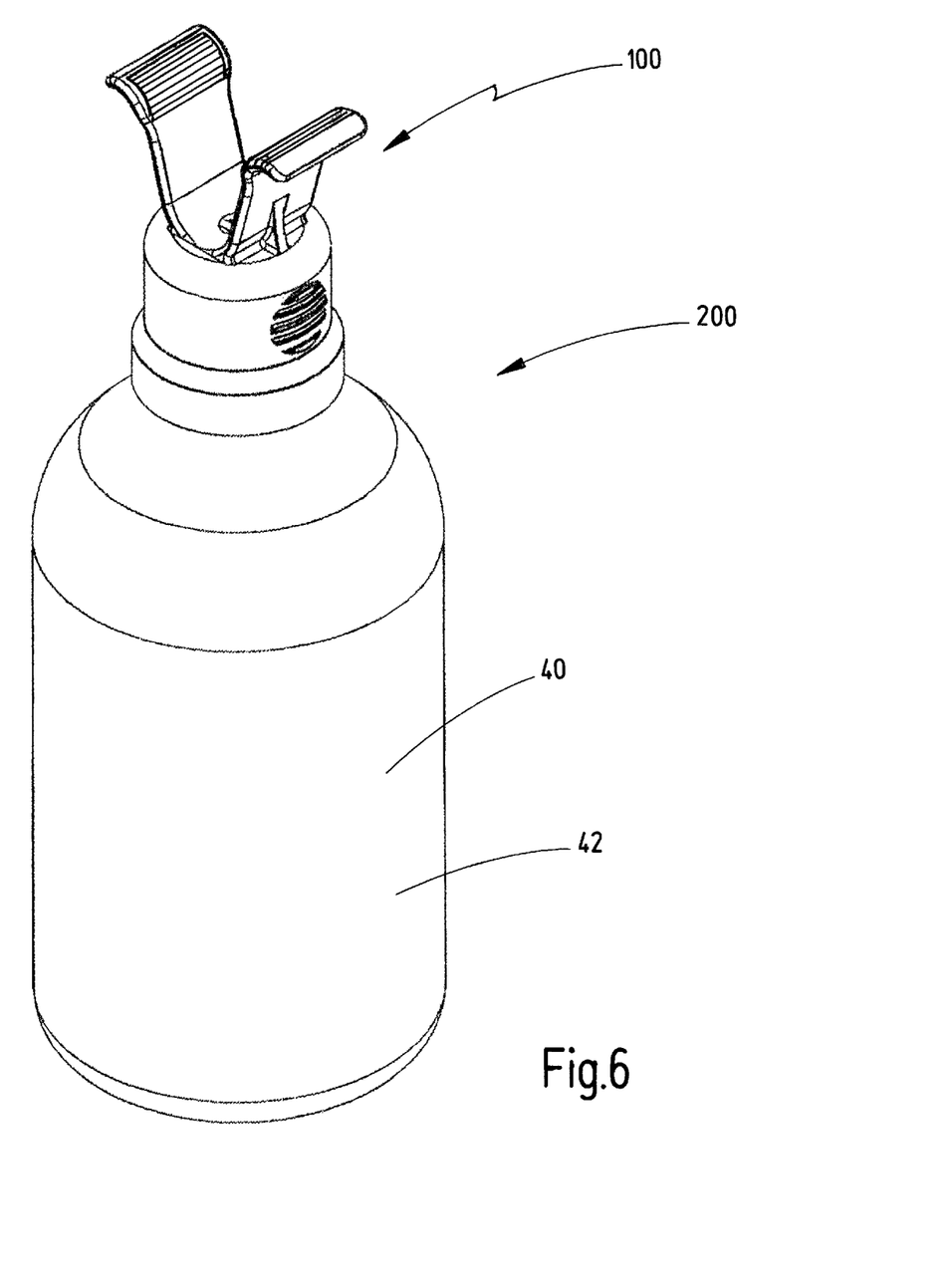
FIG. 6 is a perspective view on an eye rinsing device comprising the eye opening device according to FIGS. 1 to 5.

FIG. 6 shows a perspective view on an eye rinsing device (200) comprising the eye opening device (100) according to FIGS. 1 to 5. The eye rinsing device comprises an eye rinsing bottle (40) containing rinsing fluid. The eye rinsing bottle (40) is configured as a squeezable bottle (42).

Figure 7:
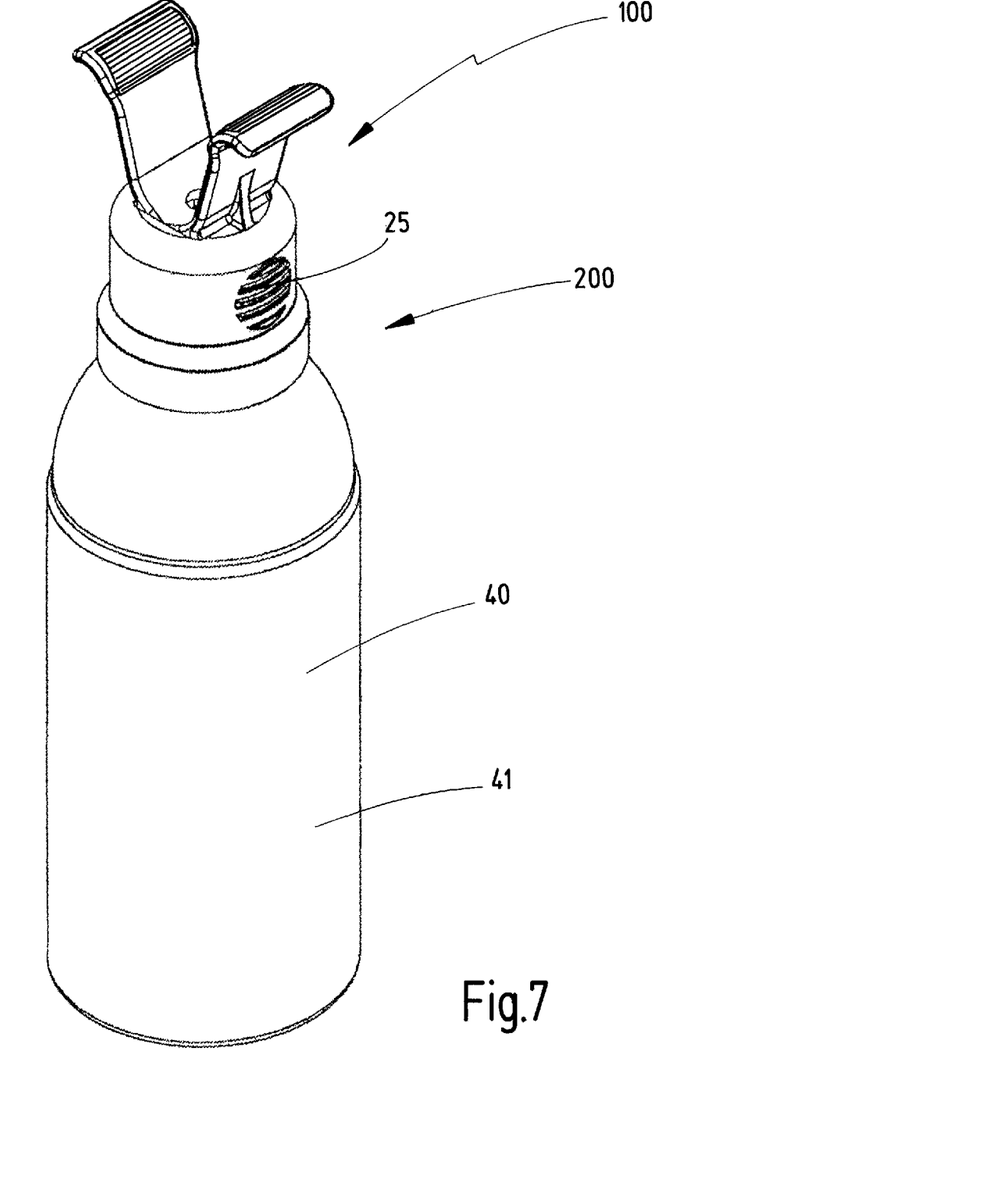
FIG. 7 is a perspective view on another eye rinsing device comprising an eye opening device according to FIGS. 1 to 5.

In FIG. 7 a perspective view on another eye rinsing device (200) comprising an eye opening device (100) according to FIGS. 1 to 5 is shown. The eye rinsing device (200) has an eye rinsing bottle (40) which is configured as a spray can (41). An actuator of the spray can (41) is disposed underneath the holding areas (25) so that the discharge of rinsing fluid can be activated by pressing the holding areas (25).

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. An eye rinsing device comprising an eye opening device for opening an eye with an upper eyelid and a lower eyelid such that the eye can be rinsed,
wherein the eye opening device comprises two wing-like spreading elements for pulling the upper eyelid and the lower eyelid of the eye apart so as to support the opening of the eye during a rinsing process,
wherein the wing-like spreading elements are configured such that two access gaps for allowing an access to the eye during the rinsing process are formed laterally between the wing-like spreading elements;
wherein the eye opening device comprises a cap-like portion, said cap-like portion comprising at least one rinsing opening for letting rinsing fluid pass towards an eye to be rinsed,
wherein each wing-like spreading elements has a first end area being attached to the cap-like portion and a second end area comprising a free end of the wing-like spreading element,
wherein the first end area and/or the second end area are configured in a curved way, wherein the width of each wing-like spreading element in the second end area is greater than the width of the wing-like spreading element in the first end area and/or the width of the wing-like spreading element in a middle area of the wing-like spreading element, and wherein each wing-like spreading element comprises a furthest point in the second end area being furthest away from the first end area of the respective wing-like spreading element, said furthest point not being the free end of the wing-like spreading element.

2. The eye rinsing device according to claim 1, wherein the eye opening device is configured as an attachment for an eye rinsing bottle of an eye rinsing device.

3. The eye rinsing device according to claim 2, wherein each wing-like spreading elements has a first end area being attached to the cap-like portion and a second end area comprising a free end of the wing-like spreading element, wherein the first end area and/or the second end area are configured in a curved way.

4. The eye rinsing device according to claim 2, wherein each wing-like spreading element is supported in longitudinal direction of the eye opening device by a lengthwise grove.

5. The eye rinsing device according to claim 1, wherein each wing-like spreading element is curved in its first end area in such a way that an imaginary secant line between two points within the first end area is disposed such that the imaginary secant line faces the other wing-like spreading element.

6. The eye rinsing device according to claim 5, wherein each wing-like spreading element is curved in its second end area in such a way that an imaginary secant line between two points within the second end area is disposed such that it faces away from the other wing-like spreading element.

7. The eye rinsing device according to claim 1, wherein each wing-like spreading element is curved in its second end area in such a way that an imaginary secant line between two points within the second end area is disposed such that it faces away from the other wing-like spreading element.

8. The eye rinsing device according to claim 1, wherein each wing-like spreading element is supported in longitudinal direction of the eye opening device by a lengthwise grove.

9. The eye rinsing device according to claim 1, wherein that each wing-like spreading element comprises a contact area for contacting a surrounding of an eye, wherein the contact area comprises a slip-resistant surface structure.

10. The eye rinsing device according to claim 1, wherein the cap-like portion comprises holding areas for holding the eye opening device, said holding areas comprising a slip-resistant surface structure.

11. The eye rinsing device according to claim 1, wherein the cap-like portion comprises at least one sealing member.

* * * * *